US012571782B2

(12) United States Patent
White et al.

(10) Patent No.:  US 12,571,782 B2
(45) **Date of Patent:  \*Mar. 10, 2026**

(54) SYSTEM AND METHOD FOR TRACKING OF CHEMICAL EXPOSURES

(71) Applicant: Volatile Analysis Corporation, Grant, AL (US)

(72) Inventors: Mitchell Ray White, Pflugertville, TX (US); Christopher P. Christenson, Sequin, TX (US)

(73) Assignee: Volatile Analysis Corporation, Grant, AL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/566,106

(22) Filed: Dec. 30, 2021

(65) Prior Publication Data

US 2022/0299491 A1     Sep. 22, 2022

Related U.S. Application Data

(63) Continuation of application No. 15/958,913, filed on Apr. 20, 2018, now Pat. No. 11,243,195.

(Continued)

(51) Int. Cl.
*G01N 31/22*         (2006.01)
*B65D 65/38*        (2006.01)
(Continued)

(52) U.S. Cl.
CPC ..........  *G01N 31/224* (2013.01); *B65D 65/38* (2013.01); *B65D 79/02* (2013.01); *G01N 31/223* (2013.01);
(Continued)

(58) Field of Classification Search
CPC .. G01N 31/224; G01N 31/223; G01N 1/2214; G01N 2033/0019; B65D 65/38;
(Continued)

(56) References Cited

U.S. PATENT DOCUMENTS 4,205,043  A  *  5/1980  Esch ..................... G01N 21/783
                                                    73/23.31
4,265,635  A        5/1981  Kring
(Continued)

FOREIGN PATENT DOCUMENTS

JP            H0749342  A      2/1995
WO      WO-2018195481 A1 * 10/2018  ............. B65D 65/38

OTHER PUBLICATIONS

KR-20160061573-A, Kim, "Container Mangement System Using a Gyro Sensor and Schock Sensor and Camera", Jun. 1, 2016. (Year: 2016).*

(Continued)

*Primary Examiner* — Kristina M Deherrera
*Assistant Examiner* — Tania Courson
(74) *Attorney, Agent, or Firm* — Butler Snow LLP; Jon E. Holland

(57)         ABSTRACT

Systems and methods are provided for tracking all chemicals, including odors, a package is exposed to throughout the shipping process. A device is attached to the package or placed within the package to extract the chemicals that are in the surrounding environment to the device. The device can extract and concentrate volatile, semi-volatile and non-volatile chemicals that the device and the corresponding package are exposed to throughout the shipping process. The extracted chemicals may then be desorbed from the device and analyzed by an analytical instrumentation method.

8 Claims, 8 Drawing Sheets

Related U.S. Application Data

(60) Provisional application No. 62/487,773, filed on Apr. 20, 2017.

(51) Int. Cl.
   *B65D 79/02* (2006.01)
   *B65D 81/26* (2006.01)
   *G01N 1/22* (2006.01)
   *G01N 33/00* (2006.01)

(52) U.S. Cl.
   CPC ........ *B65D 81/267* (2013.01); *B65D 2203/02* (2013.01); *G01N 1/2214* (2013.01); *G01N 33/0019* (2024.05)

(58) Field of Classification Search
   CPC ... B65D 79/02; B65D 81/267; B65D 2203/02
   See application file for complete search history.

(56) References Cited

U.S. PATENT DOCUMENTS

| | | | | |
|---|---|---|---|---|
| 4,772,560 | A | 9/1988 | Attar | |
| 5,106,647 | A | 4/1992 | Manning | |
| 5,633,836 | A * | 5/1997 | Langer | B41M 3/005 |
| | | | | 368/327 |
| 5,862,101 | A * | 1/1999 | Haas | G04F 13/04 |
| | | | | 368/327 |
| 6,410,332 | B1 * | 6/2002 | Desrosiers | B01L 3/5025 |
| | | | | 436/178 |
| 6,524,846 | B1 * | 2/2003 | Robinson, Jr. | C12Q 1/04 |
| | | | | 435/287.7 |
| 6,536,370 | B2 * | 3/2003 | Paton | G01N 31/229 |
| | | | | 374/102 |
| 6,916,130 | B1 * | 7/2005 | Holt | B41J 3/54 |
| | | | | 347/171 |
| 6,991,887 | B1 * | 1/2006 | Grate | G03F 7/0757 |
| | | | | 427/515 |
| 7,188,538 | B2 * | 3/2007 | Beck | G07B 17/00661 |
| | | | | 73/865.8 |
| 7,468,672 | B2 * | 12/2008 | Harden | G01N 27/622 |
| | | | | 340/573.1 |
| 7,943,091 | B2 | 5/2011 | Beck et al. | |
| 8,166,906 | B2 * | 5/2012 | Ambrozy | G01K 5/48 |
| | | | | 374/106 |
| 8,343,437 | B2 * | 1/2013 | Patel | G01D 3/10 |
| | | | | 436/2 |
| 9,029,167 | B2 * | 5/2015 | Wei | G01N 31/221 |
| | | | | 436/172 |
| 9,816,936 | B2 * | 11/2017 | Beck | G01N 21/78 |
| 10,318,604 | B2 * | 6/2019 | Braunberger | G06K 19/06037 |
| 10,371,677 | B2 * | 8/2019 | Nakada | B32B 25/08 |
| 10,816,519 | B1 * | 10/2020 | Bazemore | G01N 30/60 |
| 11,204,344 | B1 * | 12/2021 | Bazemore | G01N 30/60 |
| 11,243,195 | B2 * | 2/2022 | White | G01N 31/224 |
| 2002/0121235 | A1 * | 9/2002 | Carpenter | G01N 21/293 |
| | | | | 116/DIG. 14 |
| 2003/0075593 | A1 * | 4/2003 | Wood | B65D 27/04 |
| | | | | 229/80 |
| 2003/0080550 | A1 * | 5/2003 | Phillips | B65D 27/04 |
| | | | | 283/116 |
| 2003/0113228 | A1 * | 6/2003 | Goldsmith | G01N 33/02 |
| | | | | 436/1 |
| 2003/0140015 | A1 * | 7/2003 | Applebaum | B65D 27/04 |
| | | | | 705/406 |
| 2003/0194817 | A1 * | 10/2003 | Glynn | G01N 1/2273 |
| | | | | 422/50 |
| 2004/0079137 | A1 | 4/2004 | Radolovich | |
| 2004/0258561 | A1 * | 12/2004 | Reimer | G01N 31/224 |
| | | | | 422/400 |
| 2009/0013760 | A1 * | 1/2009 | Chiba | B32B 27/32 |
| | | | | 73/29.04 |
| 2009/0129984 | A1 | 5/2009 | Beck | |
| 2010/0251955 | A1 * | 10/2010 | Knoll | H01M 6/5044 |
| | | | | 427/258 |

OTHER PUBLICATIONS

European Office Action mailed Jul. 11, 2022.
JP Official Action mailed Mar. 22, 2022.

* cited by examiner

10

40

30

20

10

40

30

20

10
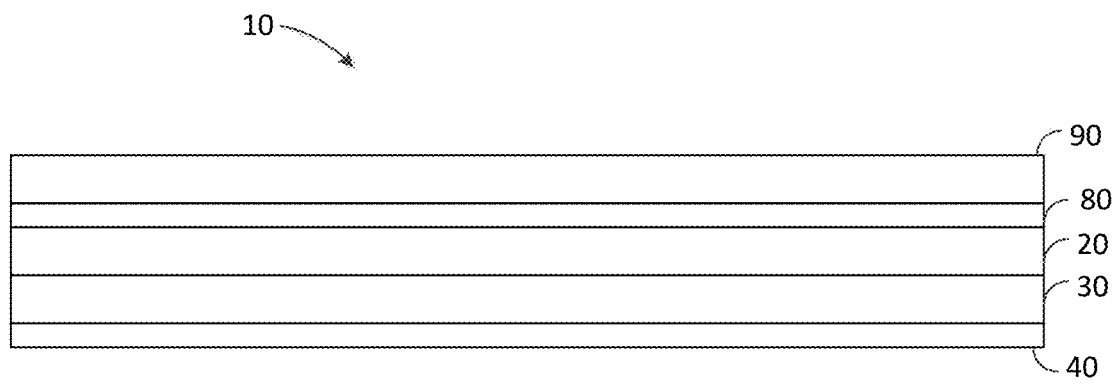
FIG. 7
10
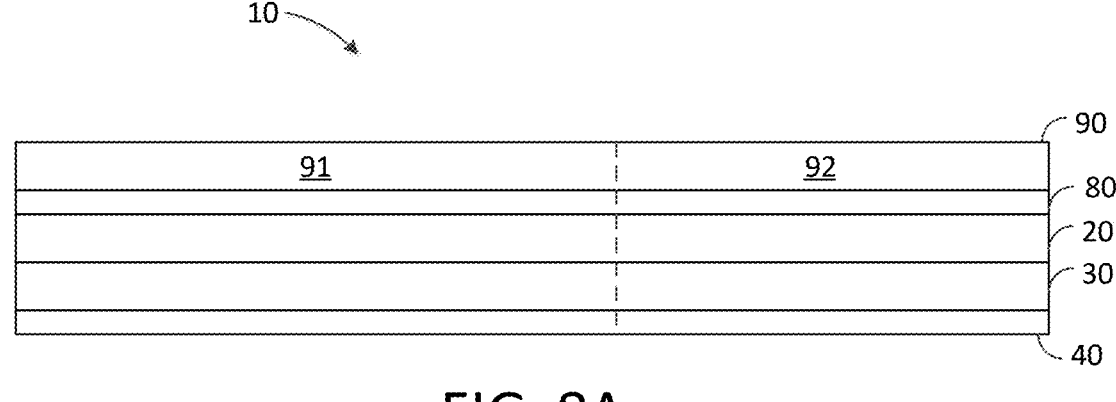
FIG. 8A
10
90
92
80
20
30
40
210          200
FIG. 8B

SYSTEM AND METHOD FOR TRACKING OF CHEMICAL EXPOSURES

CROSS REFERENCE TO RELATED APPLICATION

This application is a continuation of U.S. patent application Ser. No. 15/958,913, entitled "Systems and Methods for Tracking of Chemical and Odor Exposures" and filed on Apr. 20, 2018, which is herein incorporated by reference. U.S. application Ser. No. 15/958,913 claims priority to U.S. Provisional Application No. 62/487,773, filed Apr. 20, 2017 and entitled "Sorbent Device for Tracking of Chemical and Odor Exposures," which application is hereby incorporated by reference in its entirety.

BACKGROUND

The present application generally relates to systems and methods for detecting and tracking the chemicals and/or odors to which a package is exposed during the shipping of the package.

When shipping a package, there are many different types of events or conditions that may occur that can cause damage to the product(s) being shipped in the package. While damage to the product may be readily apparent to the recipient of the package (e.g., the package and product are crushed), many times, damage to the product is not readily apparent to the recipient. Depending on the product being shipped or transported, exposure to extreme temperatures (hot or cold), excessive shocks or vibrations, or chemicals and/or odors can damage the product in ways that may not be visible to the recipient thereby limiting the usefulness of the product. For example, prolonged exposure of fresh food products to certain odors or fumes (e.g., diesel exhaust) may result in the alteration of the taste profile of the food products.

Currently, packages being shipped can be monitored for exposure to temperature or vibration, but there is not a way to determine the chemical exposure of a package either in bulk or over time. Accordingly, a device is needed that can be placed on or in a package to determine the chemical exposure of the package by extracting volatile, semi-volatile, and non-volatile compounds (including low or trace levels) from the surrounding environment for the package.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 7 shows a side view of a second embodiment of a device in accordance with the present disclosure.

FIG. 8 shows a side view of the device of FIG. 7 with a portion of the top layer removed.

DETAILED DESCRIPTION

The present disclosure generally pertains to a chemical and odor absorbing device having of a volume of sorbent material(s) fashioned into a preselected form with specific dimensions (e.g., a patch, stripe, badge, tag, piece or tube) that attaches to or is incorporated in a package tracking label. In another embodiment, the device can be attached directly to a package, a container or space used to transport and/or store one or more packages (e.g., a delivery truck, train car, cargo hold of an airplane or ship, or an intermodal freight container), or wrapping material for one or more packages. The device may also be placed inside the container or the package (or shipping box). The sorbent material in the device extracts and concentrates volatile, semi-volatile and non-volatile chemicals (including odorous components) and hazardous volatile organic compounds from the atmosphere surrounding the package (or container) at all the locations that the package (or container) encounters throughout the shipping and storage of the package (or container) until the device is removed from the package (or container) and sealed to prevent further exposure. If the device is placed inside the container or package, any chemical that permeated through the container or package is also extracted. Chemicals that the package was exposed to throughout the shipping process may then be identified by desorbing the sorbent material in the device using appropriate techniques including thermal desorption, solvent desorption, chemical desorption, desorption by exposure to energy sources or other suitable methods. The extracted chemicals can then be analyzed by any analytical instrumentation including gas chromatography and high performance liquid chromatography, and any detector including any form of mass spectrometry (including SIFT (selected ion flow tube)), flame ionization, UV (ultraviolet), IR (infrared), or a biological or electronic nose.

A colorimetric system that cause the device to change color to reflect exposure to a single chemical, or to multiple chemicals, or chemicals present at a specific concentration may also be incorporated into the device. The observance of color changes by a micro camera can provide real time package exposure monitoring. In addition, the device permits construction of a transit diary that reflects the package's chemical exposure history throughout the shipping process, as well as chemicals that permeated the packaging material.

Figure 1:
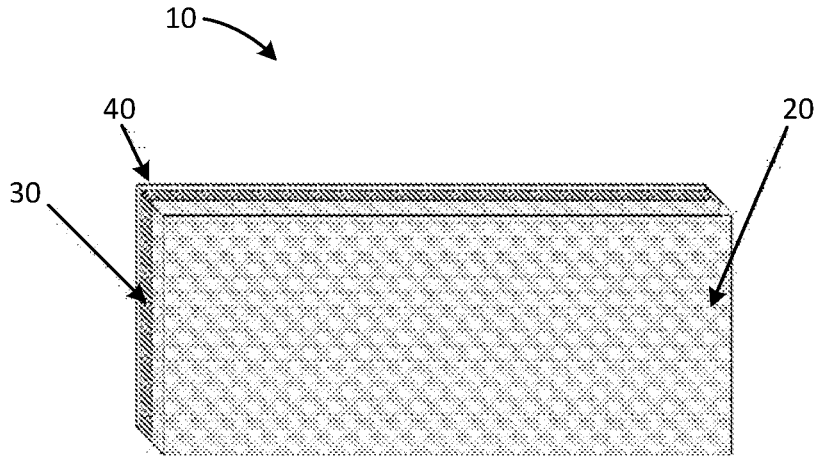
FIG. 1 shows a top view of a first embodiment of a device in accordance with the present disclosure.
Figure 2:
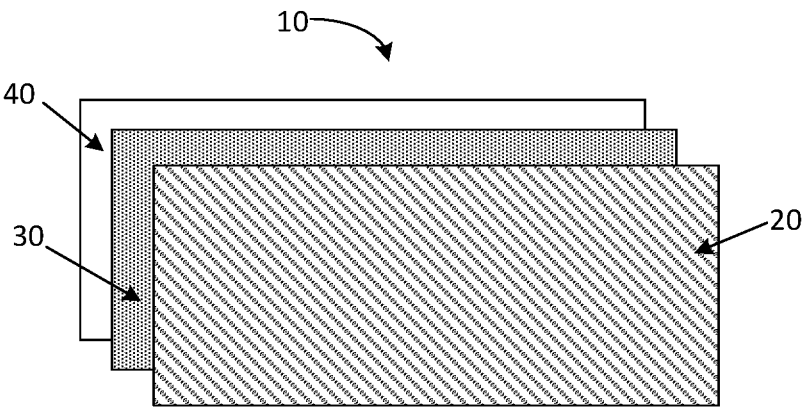
FIG. 2 shows an exploded view of the device of FIG. 1.

FIGS. 1 and 2 show a first embodiment of a device that can be attached to a shipping label for a package or the package itself to detect for chemicals in the surrounding environment of the package as the package is transported to a destination. The device 10 can include a sorbent material layer 20 bound to a metal foil layer 30. The metal foil layer 30 can include an adhesive (not shown) on a planar surface opposite the sorbent material layer 20. The adhesive may be protected by a cover 40 until the device 10 is ready to use. To place the device 10 on a shipping label or the package, the cover 40 can be removed (e.g., peeled off) and the device 10 can be attached to the shipping label or package by the adhesive on the metal foil layer 30.

The metal foil layer 30 is used to provide a base for the sorbent material layer 20 and limits the sorbent material layer to 20 to extracting chemicals via the exposed surface of the sorbent material layer 20 opposite the metal foil layer 30. In other words, the metal foil layer 30 operates to prevent the sorbent material layer 20 from extracting chemicals via the surface bound to the metal foil layer. The metal foil layer 30 can be an aluminum foil layer in one embodiment, but other non-permeable metals, alloys, plastics, ceramics, or polymers can also be used for the metal foil layer 30 in other embodiments. While the metal foil layer 30 is shown in FIGS. 1 and 2, the metal foil layer may be omitted from the device 10 and the adhesive can be applied directly to the sorbent material layer 20.

Figure 3:
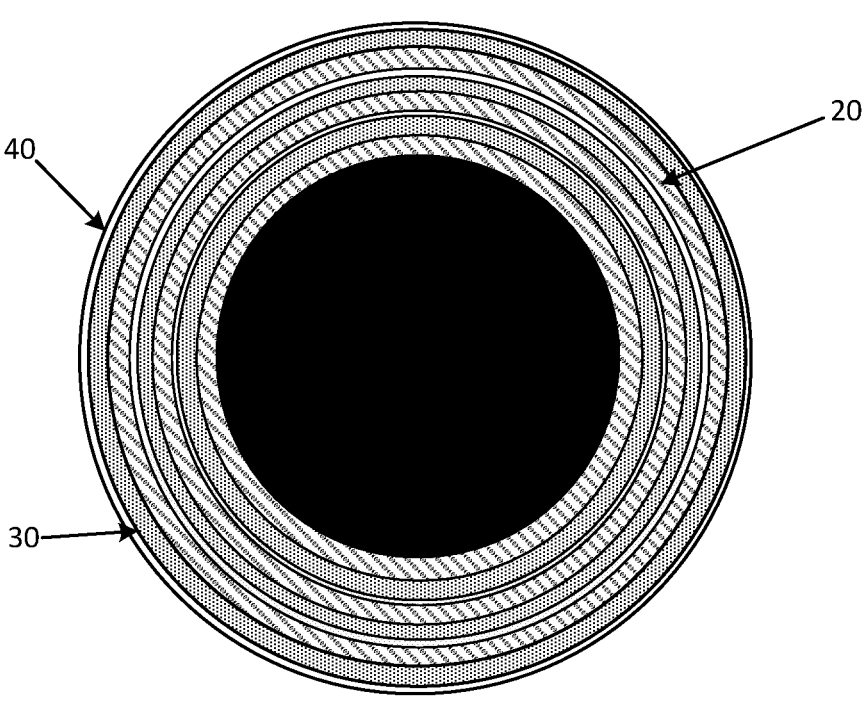
FIG. 3 shows a side view of an arrangement for storing material used for the device of FIG. 1 in accordance with an embodiment of the present disclosure.

The sorbent material layer 20 can be used to absorb and/or adsorb chemicals that may be present in the surrounding environment for the package. The sorbent material layer 20 may be a thin film in one embodiment. However, the sorbent material layer 20 may be a powder or other suitable sorbent form in other embodiments. To prevent the sorbent material layer 20 from extracting chemicals prior to being placed on the package, the sorbent material layer 20 may be protected by a second cover (not shown in FIGS. 1 and 2) similar to the metal foil layer 30. FIG. 3 shows an embodiment for storing the materials of the device 10 (i.e., the sorbent material layer 20, the metal foil layer 30 and the cover 40) in a spiral tape where the outer layers (e.g., cover 40 and metal foil layer 30) protect the inner layers (e.g., sorbent material layer 20) prior to the desired exposure period. In other embodiments, the integrity of the device 10 can be protected before application of the device 10 to the package by using impermeable packaging such as foil and glass jars.

The sorbent material layer 20 can include materials that do not have volatiles and are thermally stable, such as polydimethylsiloxane (PDMS), in one embodiment. However, in other embodiments, the sorbent material layer 20 can include, in addition to or in place of PDMS, one or more of the following: Tenax®, activated carbons (e.g., Carbo-Pack™ or Carboxen®), zeolites, Carbowax™, polyethylene (particularly low crystallinity polyethylene), polypropylene, suitable acrylates (including blends and copolymers), cellulose, papers, silica gel, alumina, zeolites (particularly large pore volume zeolites) polystyrene templated absorbents, macroporous polymer beads, natural polymers (e.g., chitin or chitosan or their derivatives), cyclodextrins or other material that may be matched via Hansen solubility parameters. In further embodiments, the sorbent material layer 20 may also include polyvinyl acetate, polyisoprene, styrene-butadiene rubber (SBR), polybutylene, polyacrylate, as well as other polymers that are known in the art, or may become known in the art. Softening agents such as microcrystalline wax may also be utilized to provide a softer, easy to mold sorbent material layer 20.

In one embodiment, the sorbent material layer 20 can target specific chemicals or classes of chemicals. In other words, the sorbent materials for the sorbent material layer 20 can be selected such that the sorbent material layer 20 is sensitive to (e.g., absorbs or adsorbs) or selects certain chemicals or classes of chemicals. For example, small fatty acids (e.g., smell of rancid butter) may be extracted and/or trapped by having an ion exchange surface on or in the sorbent material layer 20 such that when the small fatty acid is absorbed by the sorbent material layer 20, the small fatty acid is held or fixed in place in the sorbent material layer 20. Similar techniques can be used to extract and trap aldehydes, ammonias, amines or other acids in other embodiments. In one embodiment, the selection of sorbent materials may be based on the Hansen solubility parameters of the target chemicals or odors.

In another embodiment, the sorbent material layer 20 can have a sufficient volume of sorbent material to permit the sorbent material layer 20 to extract and hold a sufficient amount of chemicals to permit subsequent detection and analysis. The volume of the sorbent material can be controlled based on the surface area of the sorbent material layer 20 and the thickness of the sorbent material layer 20. The thickness of the sorbent material layer 20 can range between about 1 micron to about 2 millimeters in one embodiment, although other greater or lesser thicknesses can be used in other embodiments. The surface area for the sorbent material layer 20 can then be determined based on the selected thickness of the sorbent material layer 20 such that there is a sufficient volume of sorbent material. Alternatively, the surface area of the sorbent material layer 20 may be fixed due to placement constraints (e.g., the size of the shipping label to which the device 10 is applied). In that case, the thickness of the sorbent material layer 20 can then be determined such that there is a sufficient volume of sorbent material. In one embodiment, the dimensions for the sorbent material layer 20 and the device 10 can correspond to any shape that may be attached to a standard or oversized or undersized shipping label. In another embodiment, the sorbent material layer 20 and the device 10 may have a wedge, rectangular or cylindrical shape. In still another embodiment, the sorbent material layer 20 and the device 10 may be a wrap, similar to paper in thickness and width that can be used to wrap a package.

Figure 4:
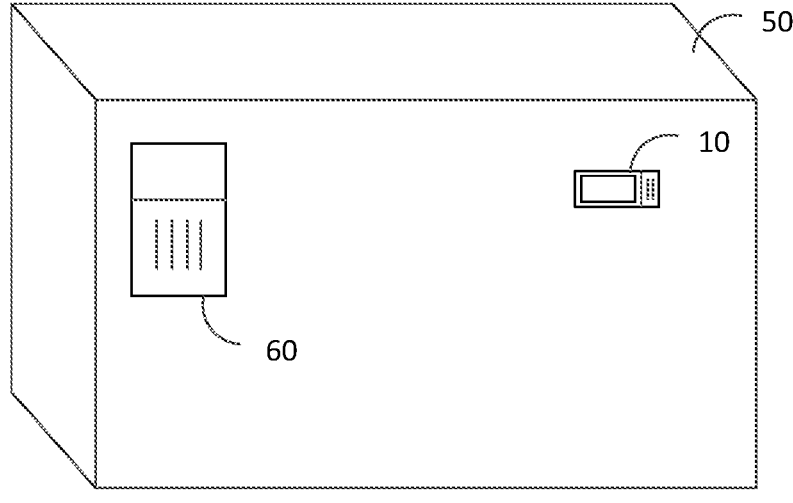
FIGS. 4-6 show front views of a package with the device of FIG. 1 positioned at different locations with respect to the package in accordance with embodiments of the present disclosure.
Figure 5:
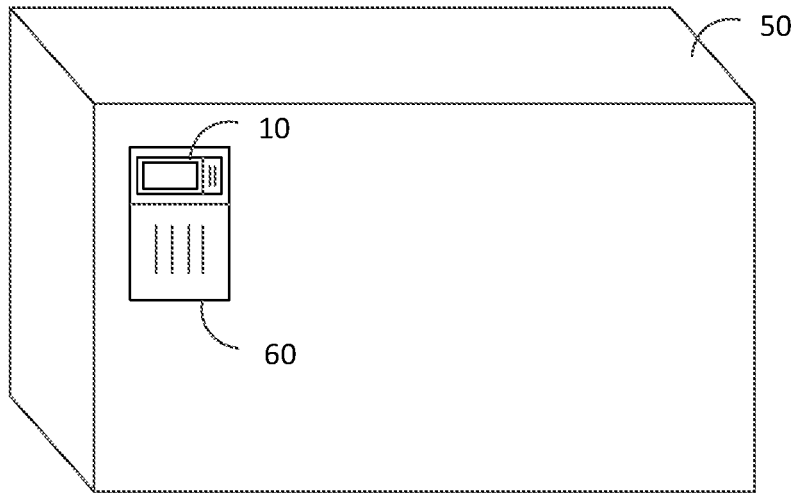
Figure 6:
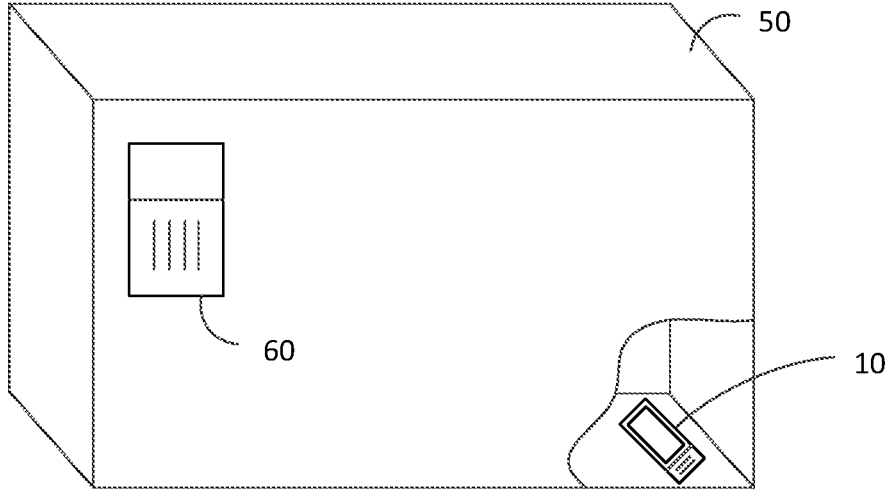

FIGS. 4-6 shows a package with the device 10 positioned at different locations with respect to the package. In FIG. 4, the device 10 is positioned on an exterior surface of the package 50, in FIG. 5, the device 10 is positioned on the shipping label 60 for the package 50, and in FIG. 6, the device 10 is positioned within the interior of the package 50. As described above, the device 10 extracts and concentrates odorous chemicals and other volatiles, semi-volatiles, and non-volatiles from the environment that the package 50 (or parcel, shipping crate or container) is exposed to throughout shipping cycle. For the embodiment of FIG. 6, the device 10 extracts and concentrates the chemicals that permeate the outer packaging or container walls of the package 50 and enter the interior of the package 50 where the product or other contents are located. In the embodiment shown in FIG. 12, the device 10 can be placed in an at least partially enclosed space 150 that can be used to transport and/or store one or more packages 50. The device 10 can be placed on a wall or other structure associated with the space 150 to extract chemicals in the environment associated with the space 150 to determine the potential chemical exposure of the package(s) 50 located in the space 150. The space 150 can be located in a cargo area of a vehicle (e.g., car, truck, plane or boat), a warehouse, a storage unit (either fixed or portable), intermodal freight carrier or other type of shipping container or storage area.

In other embodiments, the device 10 may be integrated or incorporated within the shipping label 60 (i.e., the device 10 is part of the shipping label 60) or the device 10 may be integrated or incorporated within the package 50 (i.e., the device 10 is part of the package 50). If the device 10 is incorporated within the shipping label 60 or the package 50, the device 10 may have to be removed from the shipping label 60 or package 50 prior to the device 10 being tested for exposure to chemicals. However, the device 10 may be tested for chemical exposure while remaining incorporated within the shipping label 60 or the package 50. In further embodiments, the package 50 itself may be the device 10 (i.e., the package 50 may be made from cellulose or other adsorbent materials similar to one used for the sorbent material layer 20).

FIGS. 7 and 8 show a second embodiment of the device 10. The embodiment of the device 10 shown in FIGS. 7 and 8 is similar to the embodiment shown in FIGS. 1 and 2 except that the device 10 in FIGS. 7 and 8 include a permeable layer 80 over the sorbent material layer 20 and a cover 90 to control the exposure of the permeable layer 80 and the sorbent material layer 20. The permeable layer 80 can be used to protect the sorbent material layer 20 from damage that may occur during the shipping process while still permitting chemicals to be extracted by the sorbent material layer 20. For example, the permeable layer 80 can reduce the amount of the sorbent material layer 20 that may be removed from the device 10 during a scratching event (i.e., something scratches the device 10). In one embodiment, the permeable layer 80 can be a polymer or other similar type of material.

The cover 90 can be a metal foil layer similar to metal foil layer 30 and can be used to prevent the sorbent material layer 20 from extracting chemicals from the environment prior to when the device is intended to be used. In other embodiments, either the cover 90 or the permeable layer 80 may be omitted from the device 10. If the cover 90 is not used, the device 10 can use similar storage techniques to those described above for the device of FIGS. 1 and 2 prior to the use of the device 10. In another embodiment, the cover 90 can be replaced on the permeable layer 80 when the device 10 is removed from the package 50 or to control the exposure of the sorbent material layer 20 to the environment for only specific time periods. The thickness of the sorbent material layer 20, the metal foil layer 30, the cover 40, the permeable layer 80 and the cover 90 can each range between about 1 micron to about 2 millimeters in one embodiment, although other greater or lesser thicknesses for each layer or cover can be used in other embodiments.

As shown in FIG. 8, a portion of the cover 90 can remain on the permeable layer 80 to provide a control region 200 for the device 10. The cover 90 may be configured such that the portion of the cover 90 that is not over the control region 200 can be easily removed while the remaining portion of the cover 90 can remain in position over the control region 200. The control region 200 can be used to provide a baseline for comparison with a sample region 210 (i.e., the portion of the device 10 not protected by the cover 90) of the device 10. The control region 200 can be used to prevent the erroneous detection of chemicals in the device 10 (e.g., false positives). By leaving the cover 90 over the control region 200, the sorbent material layer 20 can be prevented from extracting chemicals from the environment and can provide an indication of only those chemicals that may be present in the sorbent material layer 20 prior to the device 10 being used. Any chemicals detected in the control region 200 can be removed from or accounted for in the results of the chemicals detected in the sample region 210 to limit erroneous detections of chemicals in the sample region 210. Additionally, a controlled amount of a non-interfering compound(s)

may be placed in the sorbent material layer 20 to function as an internal standard during subsequent analysis of the material. The use of the non-interfering compound allows for estimating changes to the sample or exposed region 210 compared to the control region 200, as well as quantitating the amount of chemical exposure the package 50 experienced during transit.

In one embodiment, a non-permeable barrier can be positioned between the control region 200 and the sample region 210 perpendicular to the metal foil layer 30 to prevent contaminants from the sample region 210 from reaching the control region 200. In another embodiment, a barrier can be positioned in the sorbent material layer 20 parallel to the metal foil layer 30 to divide the sorbent material layer 20 into a sample region and a control region. If the barrier is a parallel to the metal foil layer 30, the cover 90 does not have to remain over a portion of the permeable layer 80 to provide the control region. In another embodiment, the sample region 210 and the control region 200 may be incorporated in separate devices 10 that are attached to the package 50.

Figure 9:
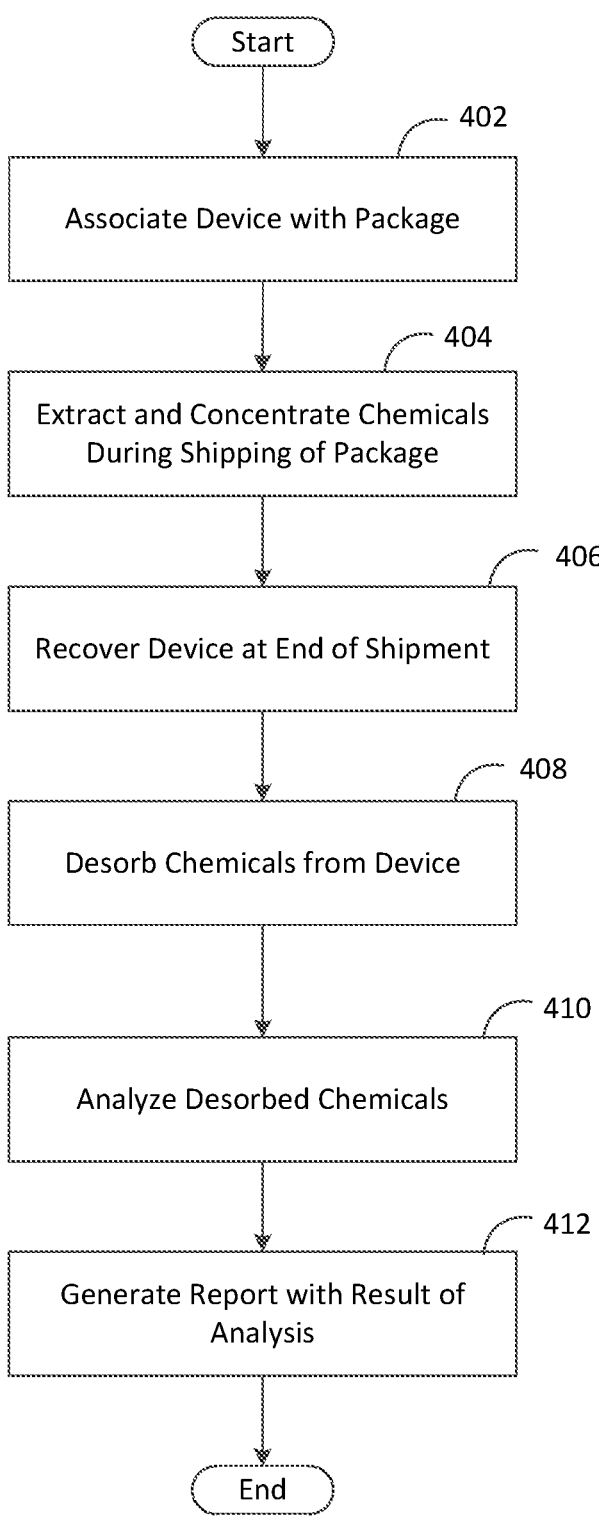
FIG. 9 is a flowchart showing an embodiment of a process for tracking chemical exposures of a package in accordance with the present disclosure.

FIG. 9 is a flowchart showing an embodiment of a process for detecting the chemical exposure of a package 50 during transit. The process can be used to ensure that a package arrives odor (or chemical) free or if an odor (or chemical) is detected that the odor (or chemical) is identified and the origin of the odor (or chemical) can be identified for liability and prevention. The process can incorporate a manual analytical system where the steps are carefully defined to ensure reproducible results. The process begins by associating the device 10 with the package 50 or container (step 402).

The device 10 may be attached to an external surface of the package to track external environmental exposures. The device 10 can be attached to the package 50 (or parcel or shipping container) or to a standard sized package shipping label placed on the package 50. In another embodiment, the device 10 may be attached inside the package 50 to detect compounds or chemicals that may permeate through the packaging, or be allowed into the package 50 through a packaging failure or breach. In a further embodiment, the device 10 may be integrated into existing shipping label systems, including but not limited to standard labels, specialty labels, and instrument systems used to track, record & report the logistics history of the package 50 (or parcel or shipping container). In still other embodiments, the sorbent material (and possibly the metal foil) of the device 10 may be incorporated into the package material or the device 10 may form the package 50 (i.e., the package material is the sorbent material (and possible the metal foil) of the device 10).

Once the device 10 is associated with the package 50, the device 10 can extract and concentrate the chemicals (including odors) or compounds that the package 50 is exposed to during the shipping of the package 50 (step 404). If the device 10 has a cover 90 protecting the permeable layer 80 and/or the sorbent material layer 20, the cover 90 has to be removed before the device 10 can start extracting and concentrating (or storing) chemicals. Moreover, regardless of which type of sorbent material is used, the sorbent material can extract and retain volatile, semi-volatile, and non-volatile molecules from the environment by absorption and adsorption. Forces and mechanisms responsible for the absorption and/or adsorption include Van der Waals forces and/or polarity. Once the package 50 has reached its destination (or the intended recipient), the device 10 can be removed from the package 50 (step 406). In one embodiment, if the sorbent material is incorporated within the package material or is the package material, the sorbent material or a portion of the sorbent material can be removed from the package material. Alternatively, the intact package material may be used instead of a portion of the package material. The removed device 10 (or sorbent material) can be placed in a sealed vessel (e.g., a sealed aluminum foil envelope or a glass jar) that prevents the device 10 (or sorbent material) from being further exposed to chemicals. The removed device 10 (or sorbent material) can then be provided to a processing facility for further processing and analysis of the removed device 10.

At the processing facility, a desorption process is then applied to the removed device 10 (or sorbent material) to desorb (or remove) the chemicals extracted and concentrated by the device 10 (step 408). The chemicals absorbed and/or adsorbed by the device 10 may be desorbed by any method including thermal desorption, solvent desorption, or desorption by exposure to different energy sources, including various forms of electromagnetic energies. For thermal desorption, the sorbent material is placed in a thermal desorption unit or heated chamber, equipped with inert gas flushing and temperature control. Upon heating the chamber, volatiles desorb from the sorbent material, are swept by inert gas (e.g., helium, nitrogen, argon) into a trap mechanism (e.g., a liquid nitrogen cooled cryo-trap, an absorbent material, or a combination thereof). The trap mechanism may be rapidly heated to release components and deposit them as a tight band on a capillary column for separation by a gas chromatograph (GC) and detection and measurement by a detector (e.g., mass spectrometer (MS), flame ionization, or flame photometric). Alternatively, the sorbent material may be desorbed by solvent and analyzed by GC or by high performance liquid chromatography (HPLC). HPLC may utilize various detectors, such as MS, infrared (IR), ultraviolet (UV), diode array, and/or other wavelength of electromagnetic radiation. In one embodiment, the chemicals may be transferred from the sorbent material to another device for introducing the extracted chemicals into analytical instrumentation.

The desorbed chemicals can then be analyzed at the processing facility to identify the specific chemicals that were present in the environment near the device 10 or to which the device 10 was exposed (step 410). Analysis of the absorbed and/or adsorbed chemicals may be accomplished through manual, partially automated, or fully automated analytical systems. Analytical separation devices to separate extracted chemicals include but are not limited to GC, HPLC, or CE (capillary electrophoresis). Analytical detection devices that detect and measure extracted chemicals include but are not limited to mass spectrometry, UV, IR, FID (flame ionization detector), AA (atomic absorption spectrophotometer), FPD (flame photometric detector), etc. In one embodiment, a GCMSO (gas chromatography-mass spectrometry-olfactometry) analysis can be performed on the desorbed chemicals. An automated analytical system where the desorption, measurement and analysis are done with minimal manual labor can be used in one embodiment.

A report can then be generated by the processing facility with the results of the analysis and provided to the user (step 412). In one embodiment, the presentation of the data can use an automated graphical presentation. In another embodiment, an automated report system can be used where the tracking and analytical data are combined and transmitted to the client with minimal manual labor. The synchronized odor and MS data can be recorded and used for the identification of the odor/molecule pairs based on a database of retention times, odor characteristics, and/or MS fragmentation patterns. In a further embodiment, the process can analyze and report the results of the analysis of the device 10 to include odor activity of extracted and analyzed molecules.

Figure 10:
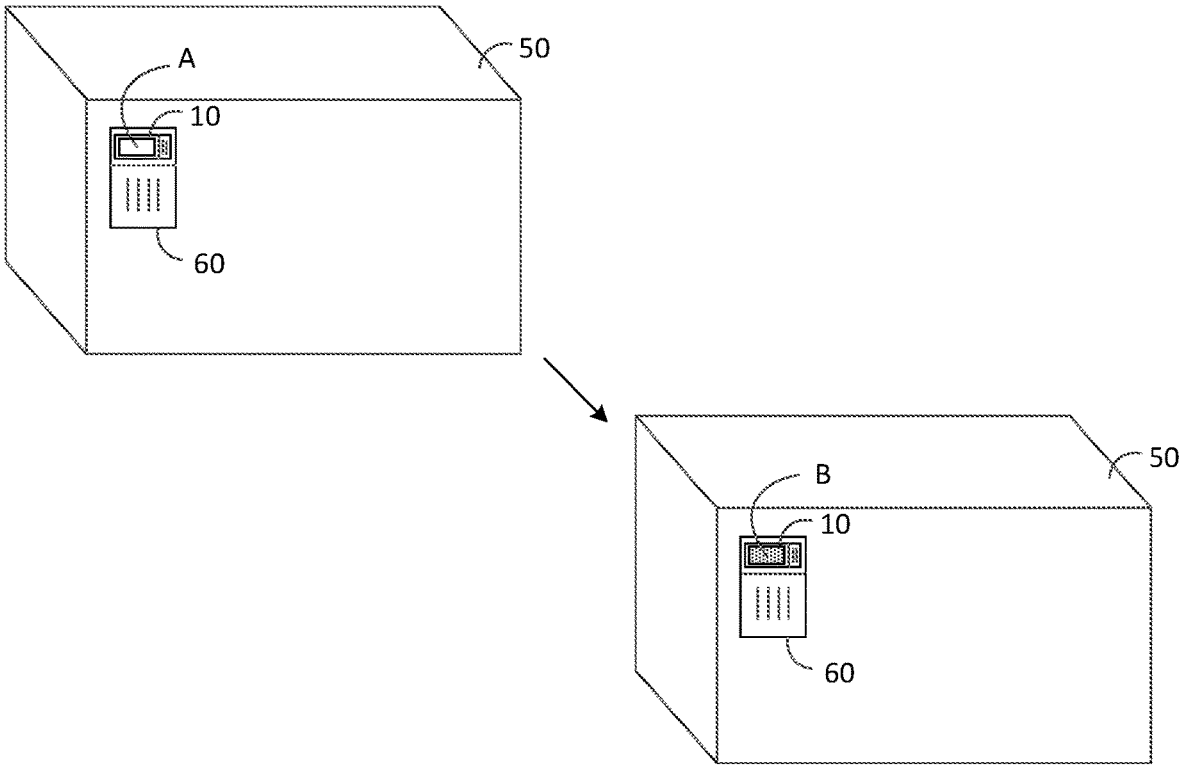
FIG. 10 shows front views of a device changing colors on a package in accordance with an embodiment of the present disclosure.
Figure 11:
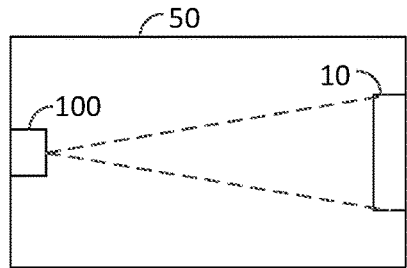
FIG. 11 shows a block diagram of a camera and device within a package in accordance with an embodiment of the present disclosure.

In an embodiment, specific chemicals or molecules extracted by the device 10 may be used to change other physical or chemical parameters and/or responses of the device 10 (specifically the sorbent material layer 20). The color, resistance and/or capacitance of the device 10 may be changed by the chemicals extracted by the device 10. For example, FIG. 10 shows the device 10 on a package 50 transitioning from a first color A to a second color B on the package 50 in response to the extraction of specific chemicals. By changing the parameters of the device 10, the device 10 can be linked to an electronic nose or other tracking/recording instrument that can be activated by the change in parameters of the device 10. In one embodiment, specific individual chemicals, or classes of chemicals, may cause the sorbent material to change color based on the presence of chemicals, or the concentration of chemicals, that the package 50 is exposed to during the shipping process. The sorbent material can include the corresponding spot test or color test material for the specific chemicals being targeted in order to trigger a color change of the sorbent material. Alternatively, the extracting and trapping of the specific chemicals may cause a change in pH that can result in a change in color of the sorbent material. In another embodiment, the monitoring of color change may be performed by a micro-camera that can capture images of the device 10 at preselected intervals. The micro-camera can either store the captured images in a non-volatile memory device for retrieval at a later time to provide passive chemical exposure monitoring or be linked with a transmission method and hardware (e.g., Bluetooth) to provide real time chemical exposure monitoring. FIG. 11 shows a block diagram of a camera 100 being positioned in a package 50 in order to monitor the device 10 for a change in color. While the camera 100 is shown on an opposite side of the package 50 from the device 10 in FIG. 11, the camera 100 can be placed at any suitable location in the package 50 that provides the camera 100 with an unobstructed view of the device 10. In other embodiments, the camera 100 can be placed in a suitable position to capture images of the device 10 regardless of where the device 10 may be positioned. If the device 10 is positioned on the exterior of the package 50, the camera 100 has to be positioned or located such that the camera can travel with the package 50 in order for the camera 100 to capture images of the device 10 during transit.

Figure 12:
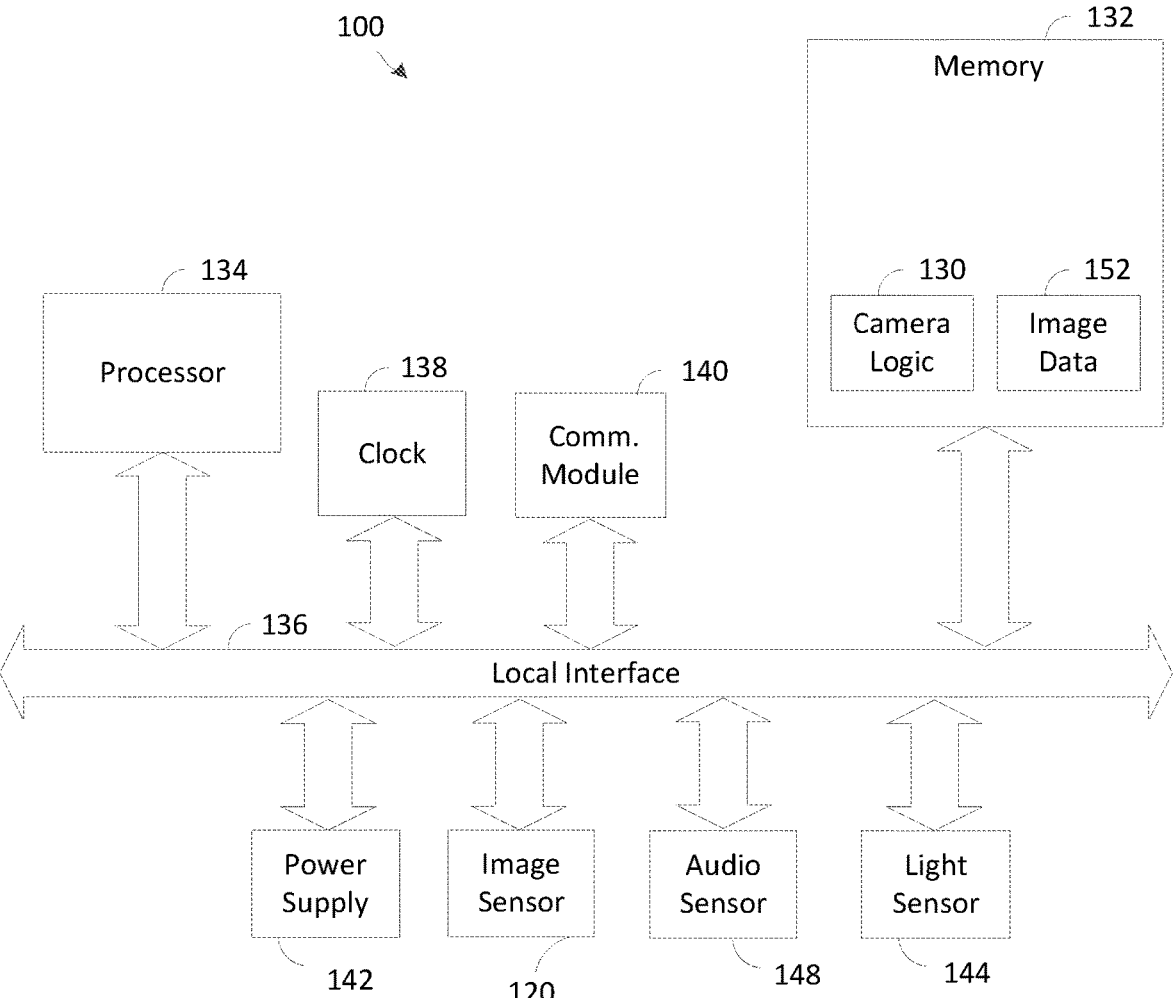
FIG. 12 is a block diagram of an embodiment of the camera of FIG. 11.
Figure 13:
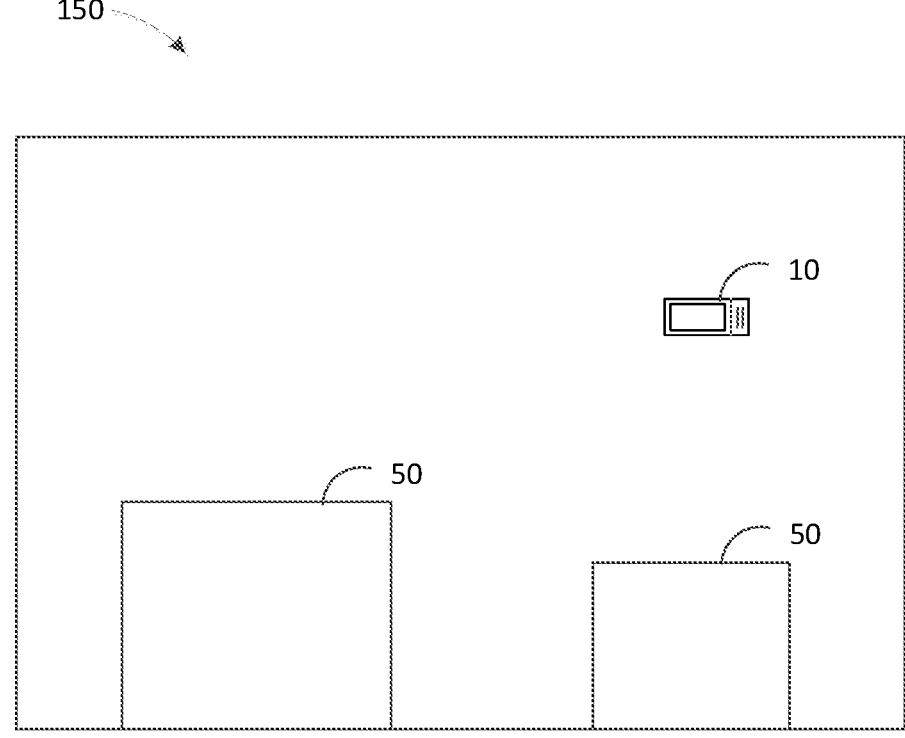
FIG. 13 shows a block diagram of the device used in a space with multiple packages in accordance with an embodiment of the present disclosure.

FIG. 12 shows an embodiment of a camera 100 that can be used to monitor device 10. The camera 100 shown in FIG. 12 can include logic 130, referred to herein as "camera logic," which may be implemented in software, firmware, hardware, or any combination thereof. In FIG. 12, the camera logic 130 is implemented in software and stored in memory 132. However, other configurations of the camera logic 130 are possible in other embodiments. The camera logic 130, when implemented in software, can be stored and transported on any computer-readable medium for use by or in connection with an instruction execution apparatus that can fetch and execute instructions.

The embodiment of the camera 100 shown in FIG. 12 can include at least one conventional processor 134, which can incorporate processing hardware for executing instructions stored in the memory 132. As an example, the processor 134 may include a central processing unit (CPU), a digital signal processor (DSP), and/or a graphic processing unit (GPU). The processor 134 can communicate to and drive the other elements within the camera 100 via a local interface 136, which can include at least one bus. The camera 100 can have a clock 138, which can be used to track time and synchronize operations with other systems used to track the transit of the package 50 (e.g., package tracking systems).

The camera 100 can have a communication module 140. The communication module 140 can include a radio frequency (RF) radio or other device for communicating wirelessly with other computing devices or package tracking systems. The power supply 142 can provide power to the other components of the camera 100 and may include a battery or other power source.

As shown by FIG. 12, the camera 100 can also include an image sensor 120, an audio sensor 148 and a light sensor 144. The image sensor 120 can be used to record, capture or obtain images or videos of the area surrounding or in proximity to the device 10. The images or videos from the image sensor 120 can be stored as image data 152 in memory 132. The audio sensor 148 or microphone can be used to record sound or noise occurring in the area surrounding or in proximity to the camera 100. The light sensor 144 can be configured to sense ambient light in the area surrounding the camera 100 and device 10 and used by processor 134 to determine when to activate a light source (not shown) to illuminate the device 10.

From time-to-time, the camera logic 130 can be configured to transmit the image data 152 to a computing device or a package tracking system. Alternatively, the image data 152 may be retrieved from camera 100 via a wired connection at the same time the device 10 is removed from the package 50 and provided to the computing device or package tracking system. The image data 152 can be time-stamped based on the time indicated by the clock 138 in order to indicate when the image data 152 was obtained. The image data 152 may be analyzed by the computing device (which can be the processor 134 in one embodiment) or package tracking system to determine if the device 10 has changed color. If the device 10 has changed color, the computing device or package tracking system can then compare the time stamp of the image data 152 to corresponding location information (e.g., GPS coordinates) for the package associated with the same time in order to identify the location where the chemical exposure occurred such that a source of the chemical exposure may be identified. In one embodiment, the image data 152 may be presented to a user for analysis or review.

In an embodiment, a time tracking mechanism can be included with or incorporated in the device 10 to record the timing of exposure events during the shipping of the package 50. The time tracking mechanism can used to provide a history of exposure information for the device 10. If the device 10 can provide an indication (e.g., a color change or property change) of when a chemical has been detected, the time tracking mechanism can be used to correlate the detection of the chemical to a specific time (and possibly location if other shipping information is available). The time tracking mechanism can include corresponding sensors, circuitry, microprocessors and/or software to detect and process the indication from the device 10. In one embodiment, the time tracking mechanism can be clock 138 incorporated in camera 100. The time tracking mechanism may use shipping information (e.g., time and location information) generated by the shipper during the transit of the package 50 to provide information on when and where the device may have been exposed to specific chemicals.

In an embodiment, the device 10 may be integrated with package tracking systems provided for the package 50. The package tracking systems can include instruments such as temperature, position or motion sensors that can detect and record circumstances associated with the transport of the package 50. The package tracking systems may passively or actively report detected conditions (including chemical exposure) to the shipper (or recipient).

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A device to detect chemical exposure of a package containing a product for shipment, the package having a shipping label positioned on an exterior surface of the package, the device comprising:
   a metal foil layer attached to the shipping label positioned on the exterior surface of the package;
   a sorbent material layer attached to the metal foil layer, the sorbent material layer comprising at least one sorbent material to extract and hold at least one chemical present in the environment surrounding the package during the shipment, wherein the sorbent material is configured to be removed and analyzed to determine the at least one chemical extracted and held by the sorbent material, the determined at least one chemical being indicative of the chemical exposure of the package during the shipment;
   a permeable layer positioned in contact with the sorbent material layer opposite the metal foil layer, the permeable layer configured to permit the at least one chemical to pass through the permeable layer to the at least one sorbent material; and
   a cover positioned in contact with the permeable layer, the cover comprising a non-permeable material configured to prevent the at least one chemical from passing through the cover, wherein the cover has a first portion that is removable from the permeable layer and a second portion configured to remain in contact with the permeable layer when the first portion is removed, and wherein an area of the sorbent material layer corresponding to the second portion is a control region for the device.

2. The device of claim 1, wherein the at least one sorbent material comprises polydimethylsiloxane.

3. The device of claim 1, wherein the at least one sorbent material is configured to change color in response to the extraction of the at least one chemical.

4. The device of claim 1, wherein the metal foil layer is attached to the shipping label with an adhesive.

5. The device of claim 4, further comprising a cover in contact with the adhesive, wherein the cover is configured to be removed from the adhesive prior to the metal foil layer being attached to the shipping label.

6. A packaging system for shipping a product, comprising:

a shipping label for use on an exterior surface of a package containing the product for shipment; and a device attached to the shipping label for detecting chemical exposure of the package during shipment of the package, the device having a metal foil layer attached to the shipping label and a sorbent material layer attached to the metal foil layer, the sorbent material layer comprising at least one sorbent material to extract and hold at least one chemical present in the environment surrounding the package, wherein the sorbent material is configured to be removed and analyzed to determine the at least one chemical extracted and held by the sorbent material, the determined at least one chemical being indicative of the chemical exposure of the package during the shipment, wherein the device has a permeable layer positioned in contact with the sorbent material layer opposite the metal foil layer, the permeable layer configured to permit the at least one chemical to pass through the permeable layer to the at least one sorbent material, wherein the device has a cover positioned in contact with the permeable layer, the cover comprising a non-permeable material configured to prevent the at least one chemical from passing through the cover, wherein the cover has a first portion that is removable from the permeable layer and a second portion configured to remain in contact with the permeable layer when the first portion is removed, and wherein an area of the sorbent material layer corresponding to the second portion is a control region for the device.

7. The system of claim 6, wherein the at least one sorbent material is configured to change color in response to the extraction of the at least one chemical.

8. A method, comprising:

providing a package containing a product to be shipped to a destination indicated by a shipping label on an exterior surface of the package, the shipping label attached to a device for detecting chemical exposure of the package during shipment of the package, the device having a metal foil layer attached to the shipping label and a sorbent material layer attached to the metal foil layer, the sorbent material layer comprising at least one sorbent material to extract and hold at least one chemical present in the environment surrounding the package, wherein the sorbent material is configured to be removed and analyzed to determine the at least one chemical extracted and held by the sorbent material, the determined at least one chemical being indicative of the chemical exposure of the package during the shipment, wherein the device has a permeable layer positioned in contact with the sorbent material layer opposite the metal foil layer, the permeable layer configured to permit the at least one chemical to pass through the permeable layer to the at least one sorbent material, wherein the device has a cover positioned in contact with the permeable layer, and wherein the cover comprises a non-permeable material configured to prevent the at least one chemical from passing through the cover;

removing a first portion of the cover from the permeable layer such that a second portion of the cover remains in contact with the permeable layer, wherein an area of the sorbent material layer corresponding to the second portion is a control region for the device; and causing the package to be shipped to the destination with the first portion removed while the second portion remains in contact with the permeable layer.

\*    \*    \*    \*    \*